United States Patent [19]

Schafer-Treffenfeldt et al.

[11] Patent Number: 5,928,518
[45] Date of Patent: Jul. 27, 1999

[54] CROSS-FLOW FILTRATION PROCESS FOR SEPARATING ORGANIC COMPOUND BY ADSORPTION ON INORGANIC SOLIDS

[75] Inventors: Wiltrud Schafer-Treffenfeldt, Obertshausen; Stefan Stockhammer, Brusno, both of Germany; Gerard Richet, Saint-Quentin; Gunter Weissland, Ham, both of France

[73] Assignee: Degussa Aktiengesellschaft, Frankfurt, Germany

[21] Appl. No.: 08/851,025

[22] Filed: May 5, 1997

[30] Foreign Application Priority Data

May 3, 1996 [DE] Germany ............... 196 17 729

[51] Int. Cl.$^6$ ................. B01D 61/00
[52] U.S. Cl. ............ 210/651; 210/650; 210/651; 210/660; 210/661; 210/670; 210/908
[58] Field of Search ............ 210/650, 651, 210/653, 661, 660, 670, 908, 644

[56] References Cited

U.S. PATENT DOCUMENTS

| | | | |
|---|---|---|---|
| 4,936,999 | 6/1990 | Mattison et al. | 210/651 |
| 5,145,584 | 9/1992 | Swamikannu | 210/651 |
| 5,233,012 | 8/1993 | Kwamura et al. | 528/161 |
| 5,364,534 | 11/1994 | Anselme | 210/650 |
| 5,366,634 | 11/1994 | Vijayan | 210/638 |
| 5,505,841 | 4/1996 | Pirbazari et al. | 210/636 |
| 5,505,842 | 4/1996 | Enderle | 210/93 |
| 5,527,958 | 6/1996 | Yonsel et al. | 562/554 |

FOREIGN PATENT DOCUMENTS

| | | |
|---|---|---|
| 0 248 524 | 12/1987 | European Pat. Off. |
| 0 351 363 A1 | 1/1990 | European Pat. Off. |
| 0 645 371 A1 | 3/1995 | European Pat. Off. |
| 40 08 983 A1 | 9/1991 | Germany |
| 43 25 937 A1 | 2/1995 | Germany |
| 2 280 430 | 2/1995 | United Kingdom |

*Primary Examiner*—Ana Fortuna
*Attorney, Agent, or Firm*—Pillsbury Madison & Sutro LLP

[57] ABSTRACT

Process for separating and/or isolating organic compounds which are soluble in water, some of which are adsorbed on finely divided inorganic solids, by adsorption of this fraction and isolation of the loaded solid, which is characterised in that a) the solutions containing the organic compounds are placed in contact with a suitable solid, then cross-flow filtration is performed by b) allowing the suspensions produced to flow alongside a porous surface/membrane, wherein c) a pressure difference is set up between the side being flowed over and the opposite side of the surface/membrane, d) so that a fraction of the solution from which adsorbable compounds (a) have been partly or completely removed and is flowing over the surface/membrane passes through the surface/membrane in a transverse direction with respect to the direction of flow (filtrate flow), e) the non-adsorbed organic compounds (b) are isolated from this fraction, f) the fraction of solution or suspension which does not pass through the surface/membrane, optionally after isolation of some or of the entire amount of the solid, is returned to circulation to adsorb residual amounts of organic compounds which are optionally still present (point a).

16 Claims, No Drawings

5,928,518

CROSS-FLOW FILTRATION PROCESS FOR SEPARATING ORGANIC COMPOUND BY ADSORPTION ON INORGANIC SOLIDS

This application is based on Application No. 196 17 729.4 filed in Germany on May 3, 1996, the content of which is incorporated hereinto by reference.

BACKGROUND OF THE INVENTION

1. Field of the Invention

The invention relates to a process for isolating organic compounds and/or separating these from each other in particular from aqueous solutions, after adsorption on inorganic solids, by cross-flow filtration.

2. Prior Art

Solutions for which the process according to the invention may be used arise, for instance, from the industrial synthesis of oligopeptides, in which sometimes not inconsiderable residual concentrations of the amino acids used as starting materials always remain in solution, together with the desired end product. A critical step in the production of pure peptides is isolation of the starting materials. Isolation of amino acids from dipeptides is especially difficult if processes of preparation are used in which the protective group required to protect the amino group is removed directly after coupling (e.g. during peptide coupling with N-carboxylic anhydrides) and a second unprotected amino acid is used for coupling. The free amino acids and free peptides present in solution in this case often have very similar pKi values and therefore very similar dissolution behaviour. Purification by crystallisation is therefore often impossible, or only possible by incurring large losses. A variety of chromatographic processes from the prior art is used for this purpose.

In the case of partition chromatography, the different partition equilibria of amino acids and peptides between two different solvent systems (aqueous and organic) is used. If these partition equilibria are not sufficiently far apart, purification by this method is difficult to impossible.

Affinity chromatography, in which differences in bonding strengths to specific reaction partners is used, is only suitable for very small concentrations.

Chromatographic processes which depend on hydrophobic interactions between a support and the substances to be purified (as are described for peptides and proteins in the PCT (SE 93/00582)) make use of the dependence of these interactions, and thus bonding to the support material, on the salt concentration in the elution medium. In these processes, the addition of non-polar, organic substances is often required in order to achieve sufficient separating power.

In comparison to the processes mentioned so far, ion-exchange chromatography is the most important with regard to industrial processes. The separation of amino acids and peptides here depends on differences in the isoelectric points of the substances. Amino acids and peptides are bonded in their cationic form by ion exchange on a cation exchanger at an acid pH. Separation is performed by elution with an increasing pH gradient in the elution medium. The individual amino acids and peptides are released and eluted at the pH which corresponds to their own isoelectric point.

All the chromatographic processes mentioned have the disadvantage that several stages are required to produce sufficient purity in the case of substances with similar and comparable functional groups. This means that several purification cycles, in which relatively large losses of valuable substance cannot be avoided, are required. In addition, the salt concentration in the solutions is sometimes increased quite considerably when eluting with the addition of salts or using a shift in pH. These salts, and possibly other additives which are required, then have to be removed again in a complicated procedure.

A further process, in which separation and purification is achieved using differences in the molecular weight and dimensions of the molecules being separated, is gel filtration. Here, a porous matrix which is generally based on organic substances is used. Larger molecules cannot diffuse into the pores and are rapidly eluted, while smaller molecules are retained. The disadvantage here, however, is the high pressure which has to be applied in order to obtain an adequate throughput.

The so-called cross-flow microfiltration process is also disclosed in the prior art, this being used, for instance, to purify beer from yeasts and solids which cause turbidity (DE-OS 4401 456).

In this process, the unclarified or pre-clarified beer flows over a porous membrane in a filter module, so that a transmembrane pressure is set up between the concentrated liquid flowing over the membrane and the filtrate on the other side. Some of the beer flowing over the membrane passes through it in a transverse direction and is collected as purified filtrate on the filtrate side. During the filtration process, the material being filtered out is sometimes deposited on the surface of the membrane as covering layer. This layer must not become too compact if passage through the membrane is to be guaranteed during the entire filtration process. In order to ensure this, the filtration process is interrupted at intervals and the covering layer on the membrane is partially dissolved using an alkaline solution.

This is one possibility of countering the unavoidable formation of covering layers on the filter itself. (Ullmann's Encyclopedia of Industrial Chemistry, vol. B2, Unit Operations 1, 5th ed. p. 10–21).

SUMMARY OF THE INVENTION

The object of the invention is to provide a process to enable the effective separation of organic compounds adsorbed on inorganic solids from each other and in particular from the compounds built up from these or containing these from aqueous or water-containing solutions. Solutions, in particular reaction mixtures which contain dipeptides or oligopeptides and the corresponding unreacted amino acids are preferably separated.

The invention provides a process for separating and/or isolating organic compounds which are soluble in water, some of which are adsorbed on finely divided inorganic solids, by adsorption of this fraction and isolation of the solid loaded with the adsorbed compound by cross-flow filtration. Solutions of organic compounds which contain, in addition to reaction products from a reaction, the unreacted organic starting compounds, are preferably treated in this way.

The process is characterised in that, a) the solutions containing the organic compounds are placed in contact with a suitable solid, b) the suspensions produced are allowed to flow alongside a porous surface/membrane, wherein c) a pressure difference is set up between the side being flowed over and the opposite side of the surface/membrane, d) so that a fraction of the solution from which adsorbable compounds have been partly or completely removed and is flowing over the surface/membrane passes through the surface/membrane in a transverse direction with respect to the direction of flow (filtrate flow), e) the non-adsorbed organic compounds are isolated from this fraction, f) the fraction of solution or suspension which does not pass through the surface/membrane, optionally after isolation of some or of the entire amount of the solid, is returned to circulation to adsorb residual amounts of organic compounds which are optionally still present (point a).

Finely divided solids are particularly suitable, such as e.g. zeolite powder, with a particle diameter of 1 to 20 µm, in particular 2 to 5 µm. These are generally used in the form of aqueous suspensions with a solids content of 5 to 60 wt. %, preferably 20 to 50 wt. %.

Low concentrations of compounds to be adsorbed generally correspond to low solids contents. When the process according to the invention is performed, there is no coating formed on the filter medium. Thus, a high resistance to filtration is also not produced. The rates of flow along the membrane are generally in the range 1 to 6 m/s, in particular 2 to 4 m/s and the transmembrane pressure varies in the range 0.2 to 3 bar, in particular 0.2 to 1.6 bar. Thus it can be shown that the filtrate flow increases with increasing rate of flow along the membrane and with increasing transmembrane pressure, wherein the last parameter has the greater effect.

Organic and inorganic ceramic filters known from the prior art for use in microfiltration and ultrafiltration are suitable as filter media. The latter are particularly suitable, as described e.g. in Ullmann's Encyclopedia, 5th ed. (op. cit.) B2, p. 10–54.

Since no covering layer is formed when using the preferably selected filtration conditions, short processing times are achieved, even with small filtration plants, due to the constant, high filtration flow.

The object of the invention is in particular to provide a process which enables effective separation of unreacted amino acids which remain in solution e.g. after preparing dipeptides or oligopeptides.

The invention also provides, therefore, a process for separating amino acids and/or aminosulphonic acids (a) present in solution and products (b) which contain these or are prepared from these, in particular dipeptides and/or oligopeptides, which is characterised in that the solutions are brought into contact with a solid suitable for use as an adsorbant, in particular a zeolite, preferably of the TA, FAU, MOR or MSI type, optionally in several steps, and the products remaining in solution are separated from the amino acids and/or aminosulphonic acids adsorbed on the solid by cross-flow filtration.

Also suitable as adsorbers are titanium silicalite or inorganic compounds of the M 41 S or MCM-41 type which have a regular mesopore structure (20–100 Å) (U.S. Pat. No. 5,098,684, J. L. Casci, Advanced Zeolite Science and Applications (Stud. Surf. Sci. Catal. 95 (1994), 329 et seq.).

The adsorption temperature may be between the melting and boiling point of the solvent being used, preferably between 15 and 35° C. The amino acids to be separated are preferably organic compounds which each contain at least one amino group and a carboxylic or a sulphonic acid group. Amino acids and/or aminosulphonic acids in which the amino and acid groups are linked by a C1–C4-alkylene group are preferred.

If the amino acids or aminosulphonic acids contain a chiral centre, the process can be applied to both enantiomers.

The amino groups may be primary, secondary or tertiary amino groups. The amino acids and aminosulphonic acids which can be separated by the process according to the invention may also contain other ftmctional groups such as, e.g. carboxyl, sulphenyl, hydroxyl, amino, thionyl, guanidine; heteroaryl. These groups may optionally also contain protective groups commonly used in peptide chemistry such as, e.g. benzyloxycarboxyl, t-butyoxycarboxyl, trifluoroacetyl, tosyl for amino groups and guanadino groups or alkyl esters for carboxyl groups. The process can be applied particularly advantageously to separating amino acids and/or aminosulphonic acids from products containing these or prepared from these when the products also contain free amino and carboxylic acid or sulphonic acid groups. The process is preferably used to separate unreacted amino acids and/or aminosulphonic acids from products which are prepared by linking two or more amino acids. Compounds in which the linkage is obtained via an amide bond are particularly preferred.

The process according to the invention is preferably applied to separating dipeptides and/or tripeptides from mainly aqueous solutions which contain some or all of the amino acids or aminosulphonic acids forming the peptides.

DETAILED DESCRIPTION OF PREFERRED EMBODIMENTS OF THE INVENTION

By way of example, the following preferably performed separations of dipeptides and the a-L-amino acids contained therein, may be mentioned:

Ala+Pro from Ala-Pro

Val+Pro from Val-Pro

Gly+Gln from Gly-Gln

Tyr+Arg from Tyr-Arg

Gly+Glu from Gly-Glu

The following is regarded as an example of separating β-L-amino acids:

β-Ala+His from β-Ala-His

The same applies to separating α-L-amino acids from solutions which contain tripeptides:

Gly+Tyr from Gly-Gly-Tyr

The following may be mentioned as an example of separating a diaminocarboxylic acid in which one amino group is protected by a trifluoroacetyl group:

ε-TFA - Lys+Pro from ε-TFA-Lys-Pro (TFA: trifluoroacetyl)

Testing the process according to the invention under conditions which approximate to those used in practice demonstrates universal applicability, although amino acids may have a number of different chemical properties.

Accordingly, peptides consisting of amino acids derived from a protein source have:

a) "hydrophobic" side chains: Gly, Ala, Pro, Val, and/or b) "polar" side chains: Tyr, Gln and/or c) "acid" side chains: Glu and/or d) "basic" side chains: Arg, Lys, as is demonstrated by the amino acids listed by way of example.

The separation of amino acids with secondary amino groups can also be achieved according to the invention, e.g.

Sar+Ala from Sar-Ala (Sar=sarcosine).

The same also applies to the separation of aminosulphonic acids, e.g.

Ala+Tau from Ala-Tau (Tau=taurine).

Since the adsorption of amino acids is possible over the entire pH range from 1 to the relevant IP, no pH correction is required in solutions with the appropriate pH.

Adsorption is preferably performed at a pH<IP (isoelectric point) whereas desorption is preferably performed at a pH>IP. If the isoelectric points of two of the amino acids or aminosulphonic acids to be removed from solution are well separated, the adsorption step is optionally repeated at different pHs.

The process is also extremely suitable for separating L-leucine and L-isoleucine, present in the same solution, from each other. The zeolite containing adsorbed L-leucine is separated from L-isoleucine, which remains in solution, by the cross-flow process (see also EP-A-0645 371).

Suitable zeolites, according to the invention, are those of the FAU, MSI or mordenite types, which have a modulus of 15 to 200. Zeolites as such are known from the prior art.

The solution to be purified is, for example, brought into contact with the zeolite by direct addition of zeolite powder to solution in a well-mixed container. Separating the purified solution of valuable substance from the zeolite powder is performed by subsequent cross-flow filtration.

The solid loaded with amino acids may be regenerated, if the separated amino acids are not intended to be recovered, by heating at temperatures between 400 and 900° C., e.g. in a rotary furnace. The adsorbed amino acids, however, may also be completely desorbed in aqueous solutions at a pH which depends on the particular amino acid, and separated from the zeolite powder by cross-flow filtration, and thus recovered. The solid may then be used again for purifying peptides.

Due to the favourable position of the adsorption equilibrium, the amino acids or aminosulphonic acids can be almost completely removed from the solution in one step when adding the corresponding amount of zeolite. Even though in many cases the valuable substance is also adsorbed in small amounts, a clear separating power between free amino acids and valuable substance is always observed.

This, inter alia, distinguishes the process according to the invention, when compared with the prior art.

In addition the process is highly efficient because when separating small amounts of secondary products or starting compounds in reaction solutions, in the way they are preferably used, from the valuable substances being purified, the adsorption agent needs no adsorption capacity for the valuable substance (here peptides), in comparison to ion-exchange chromatography. The amount of adsorbant required is governed solely by the amount of any substances to be removed.

It has proven advantageous that no salting out and only very little dilution of the valuable substance solution is required, as compared with the prior art (separation on organic ion exchangers).

The concentration of desired product which can be produced extends in general over a range of 1 wt. % to 60 wt. %, in particular 4 to 30 wt. %, with respect to the solution containing it, depending on its solubility and the particular process chosen.

The concentration of the amino acids being separated, e.g. those used as starting compounds, generally varies from a residual concentration of 0.01 g/l, found after reaction, up to the value which is determined by the solubility limit of the particular starting compound used. If the ratio of the individual compound being separated, such as e.g. amino acid (s), to the product being purified is expressed in g/l, then it is found that a range of 1:1000 to 1:1.5, in particular 1:300 to 1:1.5, can be successfully applied in the process according to the invention.

It has been shown that a filtrate flow of about 500 l/m2h can be achieved in the process according to the invention, even with 20 wt. % strength solids suspensions. This very high rate of flow corresponds almost to that of pure water. This could not have been expected.

This is also a result of the fact that no covering layer is formed in the filter module, according to the invention. The rate of filtrate flow used in accordance with the invention is generally in the range of 20 to 500 l/m2h.

Characterisation of the zeolites used corresponds to the classification by W. M. Meier, D. H. Olson, "Atlas of Zeolite Structure Types" 2nd ed., Butterworth-Heinemann, London, 1987.

This applies in particular to:

| Zeolite A | ^ | | zeolite TA |
|---|---|---|---|
| Zeolite DAY | ^ | Zeolite FAU | |
| Mordenite | ^ | | MOR |
| ZSM 5 | ^ | MSI | |

The number linked to the name of the ZSM 5 type by a hyphen, in the examples, corresponds to the particular $SiO_2/Al_2O_3$ ratio.

Purification of Ala-Pro production solution by the zeolite CFF process using the 8th of 50 cycles performed in the pilot plant as an example Amount of zeolite in the plant: 20 kg Filter area: 0.2 m$^2$ Membrane: ceramic 0. Initial status (after regeneration in the 7th cycle)

| | | inflow | in the plant | | outflow |
|---|---|---|---|---|---|
| | | | liquid | zeolite | |
| volumes | l | 0 | 26.9 | 20 kg | 0 |
| c Ala-Pro | g/l | | 0 | | |
| c Ala | g/l | | 0 | | |
| c Pro | g/l | | 0 | | |
| m Ala-Pro | g | | 0 | 0 | |
| m Ala | g | | 0 | 0 | |
| m Pro | g | | 0 | 0 | |

1. Adsorption (addition of crude solution)

| | | inflow | in the plant | | outflow |
|---|---|---|---|---|---|
| | | crude soln. | liquid | zeolite | |
| volumes | l | 20.1 | 47.1 | 20 kg | 0 |
| c Ala-Pro | g/l | 185.4 | 78.9 | | |
| c Ala | g/l | 21.1 | 0.5 | | |
| c Pro | g/l | 21.2 | 0 | | |
| m Ala-Pro | g | 3717 | 3708 | 9.0 | |
| m Ala | g | 423 | 23.5 | 399.5 | |
| m Pro | g | 425 | 0 | 425.0 | |

2. Filtration and washing

| | | inflow | in the plant | | outflow |
|---|---|---|---|---|---|
| | | | liquid | zeolite | |
| | | water | | | pure soln. 100.3 |
| volumes | l | 73.4 | 26.9 | 20 kg | |
| c Ala-Pro | g/l | 0 | 0 | | 35.2 |
| c Ala | g/l | 0 | 0 | | 0.43 |
| c Pro | g/l | 0 | 0 | | 0 |
| m Ala-Pro | g | 0 | 178 | 9 | 3530.6 |

-continued

|  |  | in the plant | | |
|---|---|---|---|---|
|  |  | inflow | liquid | zeolite | outflow |
| m Ala | g | 0 | 0 | 379.3 | 43.2 |
| m Pro | g | 0 | 0 | 425.0 | 0 |

3. Desorption

|  |  | in the plant | | |
|---|---|---|---|---|
|  |  | inflow | liquid | zeolite | outflow |
|  |  | NH3 soln. |  |  | "lost" |
| volumes | l | 141 | 26.9 | 20 kg | 141 |
| c Ala-Pro | g/l | 0 | 0 |  | 1.3 |
| c Ala | g/l | 0 | 0 |  | 2.5 |
| c Pro | g/l | 0 | 0 |  | 3 |
| m Ala-Pro | g | 0 | 0 | 0 | 178.9 |
| m Ala | g | 0 | 0 | 0 | 359.9 |
| m Pro | g | 0 | 0 | 0 | 423 |

4. Regeneration

No Ala-Pro, Ala or Pro can be detected in the outflowing regeneration solution.

Separation of leucine and isoleucine in aqueous solution by the zeolite CFF process using a complete cycle in a laboratory plant as an example Amount of zeolite in the plant: 100 g
Filter area: 0.0062 m$^2$
Filter membrane: polysulphonic acid 0. Initial status (after regeneration in the previous cycle)

|  |  | in the plant | | |
|---|---|---|---|---|
|  |  | inflow | liquid | zeolite | outflow |
| volumes | ml | 0 | 197 | 100 g | 0 |
| c Leu | g/l |  | 0 |  |  |
| c Ile | g/l |  | 0 |  |  |
| m Leu | mg |  | 0 | 0 |  |
| m Ile | mg |  | 0 | 0 |  |

1. Adsorption (addition of crude solution)

|  |  | in the plant | | |
|---|---|---|---|---|
|  |  | inflow | liquid | zeolite | outflow |
|  |  | crude soln. |  |  |  |
| volumes | ml | 208 | 405 | 100 g | 0 |
| c Leu | g/l | 22.9 | 0.3 |  |  |
| c Ile | g/l | 11.2 | 5.2 |  |  |
| m Leu | g | 4.8 | 0.2 | 4.6 |  |
| m Ile | g | 2.3 | 2.1 | 0.2 |  |

2. Filtration and washing

|  |  | in the plant | | |
|---|---|---|---|---|
|  |  | inflow | liquid | zeolite | outflow |
|  |  | water |  |  | Ile soln. 826 |
| volumes | ml | 609 | 188 | 100 g |  |
| c Leu | g/l | 0 | 0 |  |  |

|  |  | in the plant | | |
|---|---|---|---|---|
|  |  | inflow | liquid | zeolite | outflow |
| c Ile | g/l | 0 | 0.02 |  |  |
| m Leu | g | 0 | 0 | 4.6 | 0.08 |
| m Ile | g | 0 | 0.1 | 0.2 | 2.0 |

3. Desorption

|  |  | in the plant | | |
|---|---|---|---|---|
|  |  | inflow | liquid | zeolite | outflow |
|  |  | NH3-soln. |  |  | Leu soln. |
| volumes | ml | 587 | 188.0 | 100 g | 587 |
| c Leu | g/l | 0 | 0 |  | 7.5 |
| c Ile | g/l | 0 | 0 |  | 0.3 |
| m Leu | g | 0 | 0 | 0 | 4.4 |
| m Ile | g | 0 | 0 | 0 | 0.2 |

4. Regeneration

No leucine or isoleucine is detectable in the outflowing regeneration solution.

Balance

|  | inflow crude soln. | outflow Ile soln. aqu. | Leu soln. | Ile soln. & Leu soln. |
|---|---|---|---|---|
| Leu (g) | 4.8 | 0.1 | 4.4 | 4.5 |
| Ile (g) | 2.3 | 2 | 0.2 | 2.2 |
| Purity of Leu | 67.6% | 4.8% |  | 95.6% |
| Purity of Ile | 32.4% | 95.2% |  | 4.4% |

Purification of Ala-Pro production solution by the zeolite CFF process

Comparison of crude and pure product from cycle 8

|  | in 20.06 l of crude soln. | | in 100.3 l of pure soln. | |
|---|---|---|---|---|
|  | concentration | purity | concentration | purity |
| Ala-Pro | 3717 g | 81.4% | 3530.6 g | 98.8% |
| Ala | 423 g | 9.3% | 43.2 g | 1.2% |
| Pro | 425 g | 9.3% | 0 g | 0.0% |

What is claimed is:

1. A process for separating and/or isolating water-soluble organic adsorbable amino acids and/or aminosulphonic acids from a solution containing same, which includes the steps of:
   a) contacting a solution containing organic compounds selected from the group consisting of adsorbable amino acids, aminosulphonic acids, or mixtures thereof with a suitable solid selected from the group consisting of a TA, FAU, MOR or MSI type zeolite, a titanium silicalite, an inorganic compound having regular mesopores, and mixtures thereof, so that organic compounds are adsorbed onto the solid and a suspension is formed of the solution and organic compounds adsorbed onto the solid;
   b) conducting cross-flow filtration by flowing the suspension over a porous membrane;
   c) generating a transmembrane pressure differential between the side of the membrane over which the suspension is flowed and the opposite side of the membrane, wherein at least some of the organic compounds adsorbed onto the solid within the suspension flowing over the membrane are separated from the solution as the solution filters through the membrane in a transverse direction to the direction of suspension flow, and the organic compounds adsorbed onto the solid do not pass through the membrane; and d) recirculating the remaining non-filtered suspension so as to adsorb residual amounts of organic compounds which may still be present in the suspension, optionally isolating non-adsorbed organic compounds from the filtered suspension.

2. The process according to claim 1, wherein the solids have an average particle diameter of 1 to 20 μm.

3. The process according to claim 1, wherein 5 to 60 wt. % strength solids suspensions are used.

4. The process according to claim 1, wherein the transmembrane pressure is adjusted to 0.2 to 3 bar.

5. The process according to claim 1, wherein ceramic or organic membranes/porous surfaces with ultrafiltration or microfiltration properties are used.

6. The process according to claim 1, wherein a desired organic compound is isolated from the solution flowing through the porous membrane.

7. The process according to claim 1, wherein a reaction solution is used which can adsorb unreacted organic compounds and the desired product is isolated from the solution flowing through the porous membrane.

8. The process according to claim 1, wherein the products and the amino acids and/or aminosulphonic acids used as reactants are compounds which contain both amino and acid groups.

9. The process according to claim 1, wherein the products are compounds in which at least two amino acids and/or aminosulphonic acids are linked via an amide bond.

10. The process according to claim 1, wherein the amino and acid groups in the amino acids and/or aminosulphonic acids are connected by a $C_1$–$C_4$-alkylene group.

11. The process according to claim 1, wherein the dipeptides or oligopeptides obtained as products contain at least one amino acid which has a further functional group.

12. The process according to claim 1, wherein the dipeptides or oligopeptides obtained as products contain at least one amino acid with a hydrophobic sidechain.

13. The process according to claim 1, wherein the dipeptides or oligopeptides contain at least one amino acid in which the amino group is present as a primary, secondary or tertiary amine.

14. The process according to claim 1, wherein the dipeptides or oligopeptides contain amino acids whose amino groups are located in the α and/or β and/or γ-position.

15. The process according to claim 1, wherein separation is performed within the pH range in which adsorption on the solid takes place.

16. The process according to claim 1, wherein following step d) solids onto which organic compounds are adsorbed are flowed past the porous membrane in an aqueous solution with the appropriate pH and the organic compound is desorbed and separated from the solid by cross-flow filtration.

* * * * *